(12) United States Patent
Ly et al.

(10) Patent No.: US 9,945,825 B2
(45) Date of Patent: Apr. 17, 2018

(54) PREDICTIVE ANALYSIS OF COMPLEX DATASETS AND SYSTEMS AND METHODS INCLUDING THE SAME

(71) Applicant: The Boeing Company, Huntington Beach, CA (US)

(72) Inventors: Sidney Ly, Seattle, WA (US); Ali Salour, Fenton, MO (US)

(73) Assignee: The Boeing Company, Chicago, IL (US)

( * ) Notice: Subject to any disclaimer, the term of this patent is extended or adjusted under 35 U.S.C. 154(b) by 733 days.

(21) Appl. No.: 14/527,562

(22) Filed: Oct. 29, 2014

(65) Prior Publication Data

US 2016/0123938 A1 May 5, 2016

(51) Int. Cl.

| | | |
|---|---|---|
| G01N 15/00 | (2006.01) | |
| G01N 33/00 | (2006.01) | |
| G01N 15/06 | (2006.01) | |
| G01N 1/26 | (2006.01) | |
| G01N 15/14 | (2006.01) | |
| G01N 35/00 | (2006.01) | |
| G06F 11/00 | (2006.01) | |
| G01N 1/22 | (2006.01) | |

(52) U.S. Cl.
CPC ........... *G01N 33/0004* (2013.01); *G01N 1/26* (2013.01); *G01N 15/06* (2013.01); *G01N 15/1425* (2013.01); *G01N 35/00871* (2013.01); *G06F 11/00* (2013.01); *G01N 2001/2223* (2013.01); *G01N 2015/0693* (2013.01); *G01N 2015/1486* (2013.01); *G01N 2015/1488* (2013.01); *G01N 2015/1493* (2013.01); *G01N 2035/009* (2013.01); *G01N 2035/00881* (2013.01)

(58) Field of Classification Search
CPC .... G06F 11/079; G06N 99/005; G01N 15/06; G01N 2015/1486; G01N 15/02
USPC ............................................ 700/276; 702/19
See application file for complete search history.

(56) References Cited

U.S. PATENT DOCUMENTS

| | | | |
|---|---|---|---|
| 6,096,267 A | 8/2000 | Kishkovich et al. | |
| 6,207,460 B1 | 3/2001 | Kishkovich et al. | |
| 6,296,806 B1 | 10/2001 | Kishkovich et al. | |
| 8,398,753 B2 | 3/2013 | Sergi et al. | |

(Continued)

*Primary Examiner* — Jeffrey Aiello
(74) *Attorney, Agent, or Firm* — Dascenzo Intellectual Property Law, P.C.

(57) ABSTRACT

Predictive analysis of complex datasets and systems and methods including the same are disclosed herein. The methods include analyzing airborne particle count data from a cleanroom environment to predict a particle count fault condition within the cleanroom environment. The methods further include generating an airborne particle count data repository that includes particle counts within the cleanroom environment, analyzing the airborne particle count data to calculate a difference between a first rate of change and a second rate of change, and predicting the particle count fault condition responsive to the difference between the first rate of change and the second rate of change being outside a predetermined threshold range difference. The systems include computer readable storage media including computer-executable instructions that, when executed, direct a data analysis system to perform the methods. The systems also include a distributed cleanroom particle count monitoring system including a plurality of detection nodes.

18 Claims, 6 Drawing Sheets

(56) References Cited

U.S. PATENT DOCUMENTS

| | | | | |
|---|---|---|---|---|
| 2008/0243294 A1* | 10/2008 | Winkler | ............ | G05B 19/41875 |
| | | | | 700/121 |
| 2011/0229322 A1* | 9/2011 | Tadayon | ................. | F03D 1/065 |
| | | | | 416/91 |
| 2014/0306971 A1* | 10/2014 | Frascati | ................... | G06T 11/40 |
| | | | | 345/522 |

* cited by examiner

PREDICTIVE ANALYSIS OF COMPLEX DATASETS AND SYSTEMS AND METHODS INCLUDING THE SAME

FIELD

The present disclosure relates generally to the predictive analysis of complex data sets and more particularly to systems and methods that generate the complex data sets, that utilize the predictive analysis to determine control limits of the complex data sets, and/or that utilize the predictive analysis to predict fault conditions within the complex data sets.

BACKGROUND

Complex data sets may include chaotic, quasi-chaotic, and/or semi-random data sets and may be generated by a variety of industrial processes. As an example, airborne particle count data from cleanroom environments may be complex in nature. This airborne particle count data may remain relatively stable, with just a baseline noise level, for significant periods of time and then increase unexpectedly to elevated levels that may be unacceptable within the cleanroom environment.

The increase in airborne particle counts within the cleanroom environment may be caused by a variety of factors. As an example, filters that may be utilized to cleanse air that is circulated within the cleanroom environment may degrade, may decay, and/or may become clogged. As another example, a "dirty" object may be moved into the cleanroom environment and may shed particles within the cleanroom environment. As yet another example, human error may cause doors, windows, and/or other access points to the cleanroom environment to be left open, permitting particles to enter the cleanroom environment. As another example, workers may shed particles within the cleanroom environment.

The above-described sources of increased airborne particle counts may be quasi-random in nature and/or may be difficult to predict. At the same time, an elevated airborne particle count may be detrimental to work that is performed within the cleanroom environment and/or to the quality of a part that is fabricated within the cleanroom environment. With this in mind, simply observing, or measuring, an increased airborne particle count within the cleanroom environment and responding after-the-fact may be costly and/or time-consuming to a manufacturing process that is performed within the cleanroom environment. Thus, there exists a need for improved predictive analysis of complex data sets and for systems and methods that include and/or utilize the predictive analysis.

SUMMARY

Predictive analysis of complex datasets and systems and methods including the same are disclosed herein. The methods include analyzing airborne particle count data from a cleanroom environment to predict a particle count fault condition within the cleanroom environment. The methods include generating an airborne particle count data repository. The airborne particle count data repository includes particle counts within the cleanroom environment and a corresponding time stamp for each of the particle counts. Subsequent to performing the generating for a first elapsed time, the methods include selecting a first portion of the particle counts from the airborne particle count data repository. The first portion of the particle counts includes particle counts with a corresponding time stamp that is during the first elapsed time. The methods then include determining a first bin count for the first elapsed time and determining a second bin count for the first elapsed time. Subsequent to performing the generating for a second elapsed time, the methods include selecting a second portion of the particle counts from the airborne particle count data repository. The second portion of the particle counts includes particle counts with a corresponding time stamp that is during the second elapsed time. The methods then include determining a first bin count for the second elapsed time and determining a second bin count for the second elapsed time. The methods further include calculating a first rate of change between the first bin count for the first elapsed time and the first bin count for the second elapsed time. The methods also include calculating a second rate of change between the second bin count for the first elapsed time and the second bin count for the second elapsed time. The methods then include calculating a difference between the first rate of change and the second rate of change. Responsive to the difference between the first rate of change and the second rate of change being outside a predetermined threshold difference range, the methods include predicting the particle count fault condition within the cleanroom environment.

The systems include computer readable storage media including computer-executable instructions that, when executed, direct a data analysis system to perform the methods. The systems also include a distributed cleanroom particle count monitoring system. The distributed cleanroom particle count monitoring system includes a plurality of detection nodes. The plurality of detection nodes is spaced-apart within the cleanroom environment. Each of the detection nodes includes a particle sensor configured to determine a particle count within a respective air volume of a respective node location within the cleanroom environment. Each of the detection nodes also includes a transmitter configured to generate a particle count signal that is indicative of the particle count within the respective air volume. The distributed cleanroom particle count monitoring system also includes a receiver, which is configured to receive a plurality of respective particle count signals from the plurality of detection nodes, a data analysis system, which is programmed to analyze the plurality of respective particle count signals, and a data storage device, which is configured to store the plurality of respective particle counts.

DESCRIPTION

Figure 1:
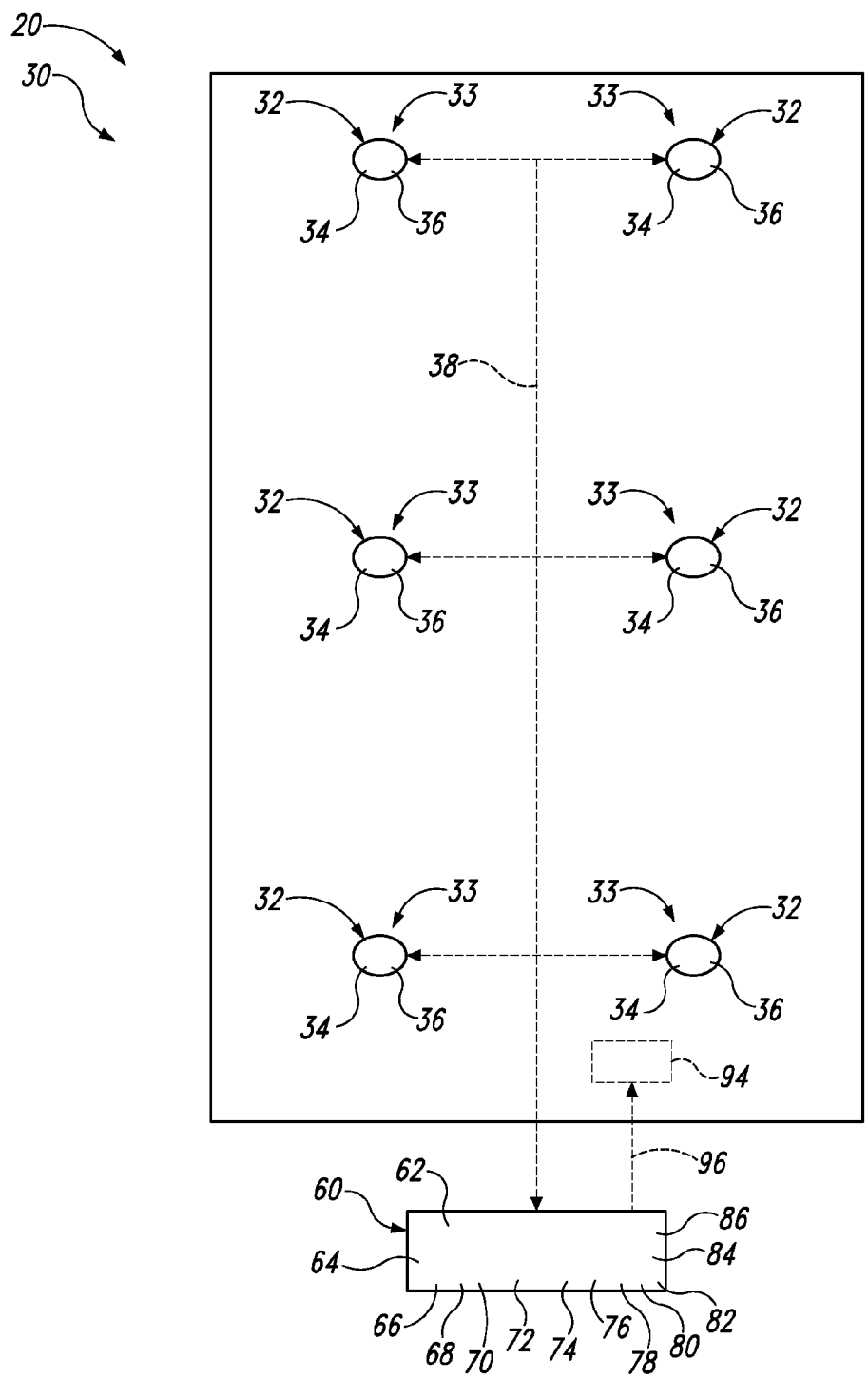
FIG. 1 is a schematic top view of a cleanroom environment that includes a distributed cleanroom particle count monitoring system according to the present disclosure.

FIGS. 1-8 provide examples of cleanroom environments 20, of distributed cleanroom particle count monitoring systems 30, of airborne particle count data 40, of methods 100/200 of analyzing the airborne particle count data, and/or of plots that may be created while performing methods 100/200 according to the present disclosure. Elements that serve a similar, or at least substantially similar, purpose are labeled with like numbers in each of FIGS. 1-8, and these elements may not be discussed in detail herein with reference to each of FIGS. 1-8. Similarly, all elements may not be labeled in each of FIGS. 1-8, but reference numerals associated therewith may be utilized herein for consistency. Elements, components, and/or features that are discussed herein with reference to one or more of FIGS. 1-8 may be included in and/or utilized with any of FIGS. 1-8 without departing from the scope of the present disclosure.

In general, elements that are likely to be included in a given (i.e., a particular) embodiment are illustrated in solid lines, while elements that are optional to a given embodiment are illustrated in dashed lines. However, elements that are shown in solid lines are not essential to all embodiments, and an element shown in solid lines may be omitted from a given embodiment without departing from the scope of the present disclosure.

FIG. 1 is a schematic top view of a cleanroom environment 20 that includes a distributed cleanroom particle count monitoring system 30 according to the present disclosure. Distributed cleanroom particle count monitoring system 30 also may be referred to herein as monitoring system 30 and/or as system 30 and includes a plurality of detection nodes 32. Detection nodes 32 are spaced-apart within cleanroom environment 20 at a plurality of separate and/or respective node locations 33. Each detection node 32 includes a particle sensor 34 and a transmitter 36. Particle sensors 34 are configured to determine a particle count at a respective node location 33 and/or within a respective air volume of the respective node location. Transmitters 36 are configured to generate a particle count signal 38 that is indicative of the particle count at the respective node location and/or within the respective air volume. Additional examples of components that may be included in and/or utilized with systems 30 according to the present disclosure are disclosed in U.S. patent application Ser. Nos. 08/795,949, 09/232,199, 08/996,790, and 11/628,576, the complete disclosures of which are hereby incorporated by reference.

System 30 further includes a receiver 62. Receiver 62 is configured to receive particle count signals 38 from detection nodes 32. Receiver 62 may form a portion of and/or may be in communication with a data analysis system 60. Data analysis system 60 is adapted, configured, designed, constructed, and/or programmed to analyze particle count signals 38 to determine corresponding particle counts that are measured by detection nodes 32. System 30 and/or data analysis system 60 thereof also includes a data storage device 64. Data storage device 64 is configured to store, remember, and/or retain the particle counts that are measured by detection nodes 32.

During operation of cleanroom environment 20 and/or distributed cleanroom particle count monitoring system 30, system 30 may be configured to repeatedly, systematically, periodically, and/or continuously measure particle counts at node locations 33 via nodes 32 and to store the particle counts utilizing data storage device 64. Thus, system 30 may generate an airborne particle count data repository. The airborne particle count data repository may include (or the airborne particle count data repository may be configured to store) a plurality of particle counts measured within cleanroom environment 20, node locations 33 where each of the particle counts was measured, and/or timestamps for (or measurement times of) each of the particle counts. As discussed in more detail herein with reference to methods 100, 200, system 30 may be adapted, configured, designed, constructed, and/or programmed to predict and/or anticipate a particle count fault condition within cleanroom environment 20 based, at least in part, on the airborne particle count data repository.

As illustrated in dashed lines in FIG. 1, system 30 further may include a notification system 94. Notification system 94 may be in communication with system 30 and/or with data analysis system 60 thereof and may be configured to notify a user of the particle count fault condition that is predicted by the airborne particle count data repository and/or by a plurality of respective particle counts that are stored within the airborne particle count data repository. As an example, data analysis system 60 may be configured to generate a fault indication signal 96 responsive to predicting the particle count fault condition. Notification system 94 may be configured to receive fault indication signal 96 and notify the user of the predicted particle count fault condition responsive to receipt of fault indication signal 96. Examples of notification system 94 include any suitable alert mechanism, including any suitable alarm, buzzer, light, strobe light, color-coded display, graphical display, and/or alphanumeric display that may be indicative of the particle count fault condition.

Detection nodes 32 may be configured to detect and/or determine the particle count within a respective air volume that is proximal thereto with any suitable frequency. As an example, detection nodes 32 may continuously, or at least substantially continuously, determine the particle count. As another example, detection nodes 32 may be configured to determine the particle count with at least a threshold particle count frequency. Examples of the threshold particle count frequency include threshold particle count frequencies of at least once per 1 second interval, at least once per 5 second interval, at least once per 10 second interval, at least once per 30 second interval, at least once per 1 minute interval, at least once per 5 minute interval, at least once per 10 minute interval, at least once per 15 minute interval, at least once per 30 minute interval, at least once per 1 hour interval, at least once per 2 hour interval, and/or at least once per 4 hour interval.

As discussed, detection nodes 32 may be spaced apart within cleanroom environment 20. This may include detection nodes 32 being spaced apart in a two-dimensional or three-dimensional detection node array. As such, each detection node 32 may be configured to detect and/or monitor the particle count in a corresponding portion of cleanroom environment 20, and the plurality of detection nodes 32 may be utilized to provide information regarding a spatial distribution of particles within cleanroom environment 20. Examples of spacing between detection nodes 32 includes spacings in which each detection node 32 is spaced apart from a nearest other detection node 32 by a distance of at least 1 meter, at least 2.5 meters, at least 5 meters, at least 7.5 meters, and/or at least 10 meters. Additionally or alternatively, each detection node may be spaced apart from the nearest other detection node by less than 30 meters, less than 25 meters, less than 20 meters, less than 15 meters, less than 10 meters, and/or less than 5 meters.

Particle sensor 34 may include any suitable structure that may be adapted, configured, designed, and/or constructed to detect airborne particles, or particulate matter, within cleanroom environment 20 and/or within the respective air volume that is proximal to particle sensor 34. This may include particle sensors 34 that detect the airborne particles via light scattering, light obscuration, and/or direct imaging.

It is within the scope of the present disclosure that particle sensor 34 simply may detect, or count, the airborne particles; however, it is also within the scope of the present disclosure that particle sensor 34 may be configured to detect, or count, particles in specific size ranges. As an example, particle sensor 34 may be configured to detect particles of less than a threshold size, such as particles of less than 0.5 micrometers in size. As another example, particle sensor 34 at least may be configured to detect particles of greater than the threshold size, such as particles of greater than 0.5 micrometers in size. As yet another example, particle sensor 34 may be configured to detect both particles of less than the threshold size and particles of greater than the threshold size and may output separate particle count signals 38 for each of the detected particle size ranges.

Transmitter 36 may include any suitable structure that may be adapted, configured, designed, and/or constructed to generate particle count signal 38 based, at least in part, on the particle count that is determined by particle sensor 34. Similarly, receiver 62 may include any suitable structure that may be adapted, configured, designed, and/or constructed to receive particle count signal 38 and/or to convey particle count signal 38 to data analysis system 60. As an example, transmitter 36 may include and/or be a wireless transmitter 36 that is configured to generate a wireless particle count signal 38. As another example, transmitter 36 may include and/or be a wired transmitter 36 that is configured to generate a wired particle count signal 38. Similarly, receiver 62 may include and/or be a wireless receiver 62 that is configured to receive the wireless particle count signal 38 and/or a wired receiver 62 that is configured to receive the wired particle count signal 38.

Data analysis system 60 may include any suitable structure that may be configured to receive the plurality of respective particle count signals 38, to determine the plurality of respective particle counts based upon the plurality of respective particle count signals, to control the operation of at least a portion of distributed cleanroom particle count monitoring system 30, and/or to perform methods 100 and/or 200, which are discussed in more detail herein. As an example, data analysis system 60 may be adapted, configured, designed, and/or programmed to predict the particle count fault condition based, at least in part, on the particle counts that are measured by system 30.

Data analysis system 60 may include any suitable structure. As an example, data analysis system 60 may include a communications framework 66. Communications framework 66 may provide communications between a processor unit 68, a memory 70, persistent storage 72, a communications unit 74, an input/output (I/O) unit 76, and/or a display 78. Memory 70, persistent storage 72, communications unit 74, input/output (I/O) unit 76, and display 78 are examples of resources accessible by processor unit 68 via communications framework 66.

Processor unit 68 serves to run instructions that may be loaded into memory 70. Processor unit 68 may include a number of processors, a multi-processor core, or some other type of processor, depending on the particular implementation. Further, processor unit 68 may be implemented using a number of heterogeneous processor systems in which a main processor is present with secondary processors on a single chip. As another illustrative example, processor unit 68 may be a symmetric multi-processor system containing multiple processors of the same type.

Memory 70 and persistent storage 72 are examples of data storage devices 64. A data storage device is any piece of hardware that is capable of storing information, such as, for example, without limitation, data, program code in functional form, and other suitable information either on a temporary basis or a permanent basis.

Data storage devices 64 also may be referred to herein as computer readable storage devices and/or as computer readable storage media 84 in these examples. Memory 70, in these examples, may be, for example, a random access memory or any other suitable volatile or non-volatile storage device. Persistent storage 72 may take various forms, depending on the particular implementation.

For example, persistent storage 72 may contain one or more components or devices. For example, persistent storage 72 may be a hard drive, a flash memory, a rewritable optical disk, a rewritable magnetic tape, or some combination of the above. The one or more components or devices used by persistent storage 72 also may be removable. For example, a removable hard drive may be used for persistent storage 72.

Communications unit 74, in these examples, provides for communications with other data processing systems or devices. In these examples, communications unit 74 may be a network interface card. Communications unit 74 may provide communications through the use of either or both physical and wireless communications links.

Input/output (I/O) unit 76 allows for input and output of data with other devices that may be connected to data analysis system 60. For example, input/output (I/O) unit 76 may provide a connection for user input through a keyboard, a mouse, and/or some other suitable input device. Further, input/output (I/O) unit 76 may send output to a printer, to display 78, and/or to notification system 94. Display 78 provides a mechanism to display information to a user.

Instructions for the operating system, applications, and/or programs may be located in data storage devices 64, which may be in communication with processor unit 68 through communications framework 66. The instructions may be in a functional form on persistent storage 72. These instructions may be loaded into memory 70 for execution by processor unit 68. The processes of the different embodiments may be performed by processor unit 68 using computer-implemented instructions, which may be located in a memory, such as memory 70.

These instructions are referred to as program instructions, a program code 80, computer usable program code, or computer readable program code that may be read and/or executed by a processor in processor unit 68. The program code in the different embodiments may be located, stored, and/or embodied on different physical or computer readable storage media, such as memory 70 or persistent storage 72.

Program code 80 may be located in a functional form on computer readable media 82 that may be selectively removable and may be loaded onto or transferred to data analysis system 60 for execution by processor unit 68. Program code 80 and computer readable media 82 may form a computer program product in these examples. In one example, computer readable media 82 may be computer readable storage media 84 or computer readable signal media 86.

Computer readable storage media 84 may include, for example, an optical or magnetic disk that is inserted or placed into a drive or other device that is part of persistent storage 72 for transfer onto a storage device, such as a hard drive, that is part of persistent storage 72. Computer readable storage media 84 also may take the form of a persistent storage, such as a hard drive, a thumb drive, or a flash memory, that is connected to data analysis system 60. In some instances, computer readable storage media 84 may not be removable from data analysis system 60.

Computer readable storage media 84 is a physical or tangible storage device used to store program code 80 rather than a medium that propagates or transmits program code 80. Computer readable storage media 84 is also referred to as a computer readable tangible storage device or a computer readable physical storage device. In other words, computer readable storage media 84 is a media that can be touched by a person.

Alternatively, program code 80 may be transferred to data analysis system 60 using computer readable signal media 86. Computer readable signal media 86 may be, for example, a propagated data signal containing program code 80. For example, computer readable signal media 86 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 80 may be downloaded over a network to persistent storage 72 from another device or data processing system through computer readable signal media 86 for use within data analysis system 60. For instance, program code stored in a computer readable storage medium in a server data processing system may be downloaded over a network from the server to data analysis system 60. The data processing system providing program code 80 may be a server computer, a client computer, or some other device capable of storing and transmitting program code 80.

The different components illustrated for data analysis system 60 are not meant to provide architectural limitations to the manner in which different embodiments may be implemented. The different illustrative embodiments may be implemented in a data processing system including components in addition to and/or in place of those illustrated for data analysis system 60. Other components shown in FIG. 1 can be varied from the illustrative examples shown. The different embodiments may be implemented using any hardware device or system adapted, configured, designed, constructed, and or programmed to run program code 80. As one example, data analysis system 60 may include organic components integrated with inorganic components and/or may be comprised entirely of organic components excluding a human being. For example, a storage device may be comprised of an organic semiconductor.

In another illustrative example, processor unit 68 may take the form of a hardware unit that has circuits that are manufactured or configured for a particular use. This type of hardware may perform operations without needing program code to be loaded into a memory from a storage device to be configured to perform the operations.

For example, when processor unit 68 takes the form of a hardware unit, processor unit 68 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a field programmable logic array, a field programmable gate array, and other suitable hardware devices. With this type of implementation, program code 80 may be omitted, because the processes for the different embodiments are implemented and/or embedded in a hardware unit.

In still another illustrative example, processor unit 68 may be implemented using a combination of processors found in computers and hardware units. Processor unit 68 may have a number of hardware units and a number of processors that are configured to run program code 80. With this example, some of the processes may be implemented and/or embedded in the number of hardware units, while other processes may be implemented in the number of processors.

In another example, a bus system may be used to implement communications framework 66 and may be comprised of one or more buses, such as a system bus or an input/output bus. Of course, the bus system may be implemented using any suitable type of architecture that provides for a transfer of data between different components or devices attached to the bus system.

Additionally, communications unit 74 may include a number of devices that transmit data, receive data, or both transmit and receive data. Communications unit 74 may be, for example, a modem or a network adapter, two network adapters, or some combination thereof. Further, communications unit 74 may include a memory that may be, for example, memory 70, or a cache, such as that found in an interface and memory controller hub that may be present in communications framework 66.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

Figure 2:
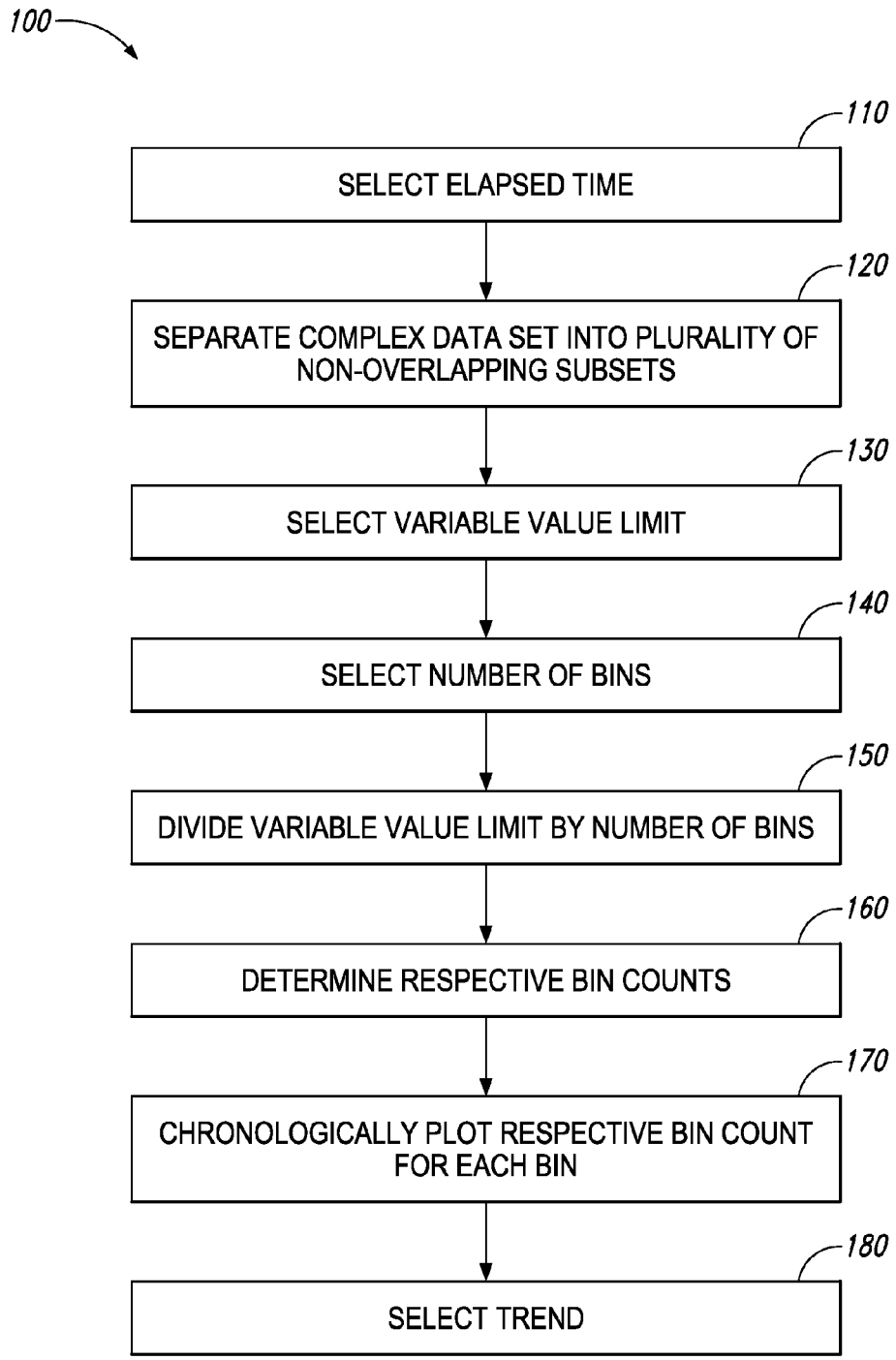
FIG. 2 is a flowchart depicting a method, according to the present disclosure, of determining predictive limits to predict a fault condition for a time-based complex data set.
Figure 3:
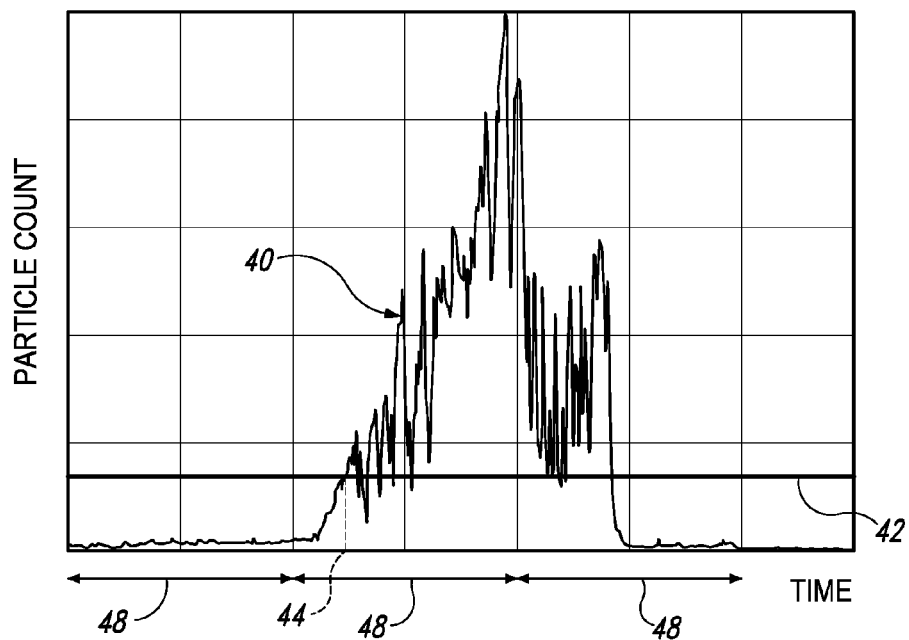
FIG. 3 is a plot of an example of airborne particle count data that may be generated by a distributed cleanroom particle count monitoring system.
Figure 4:
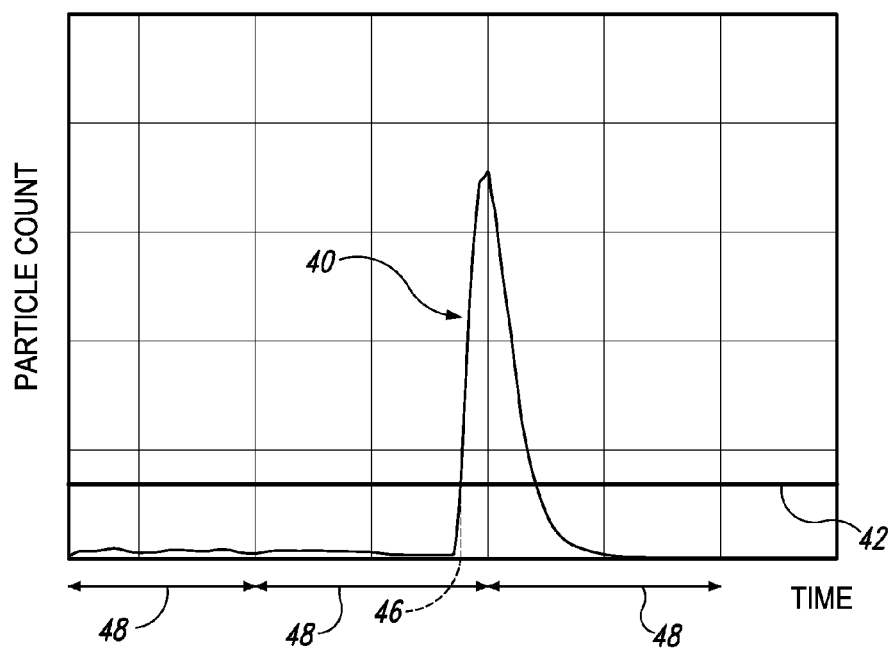
FIG. 4 is a plot of an example of airborne particle count data that may be generated by a distributed cleanroom particle count monitoring system.
Figure 5:
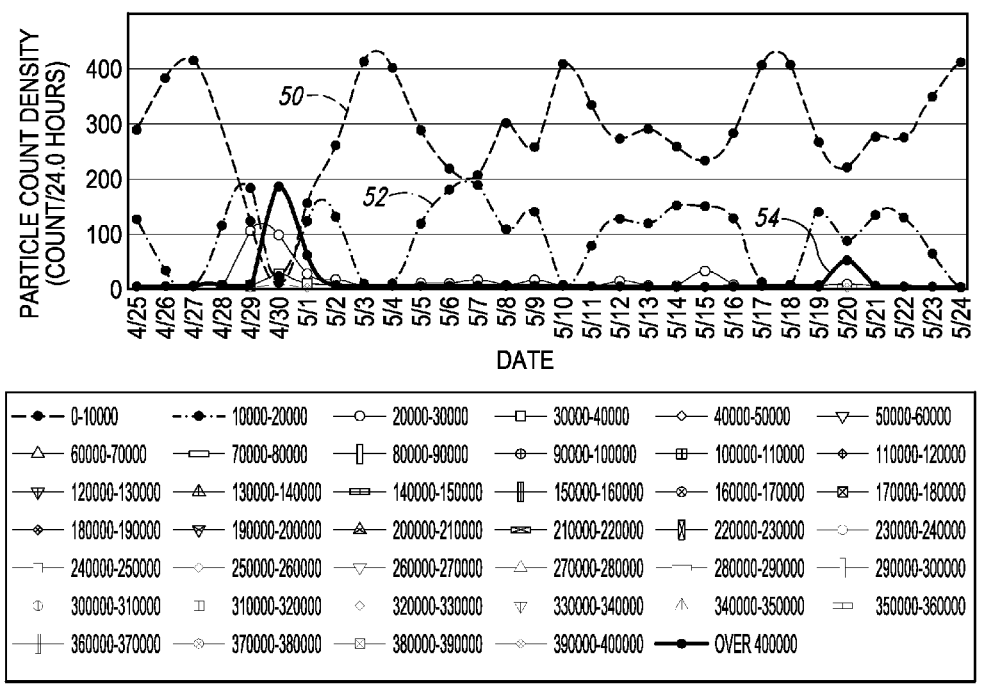
FIG. 5 is a plot of an example of a binning process that may be utilized to analyze airborne particle count data.
Figure 6:
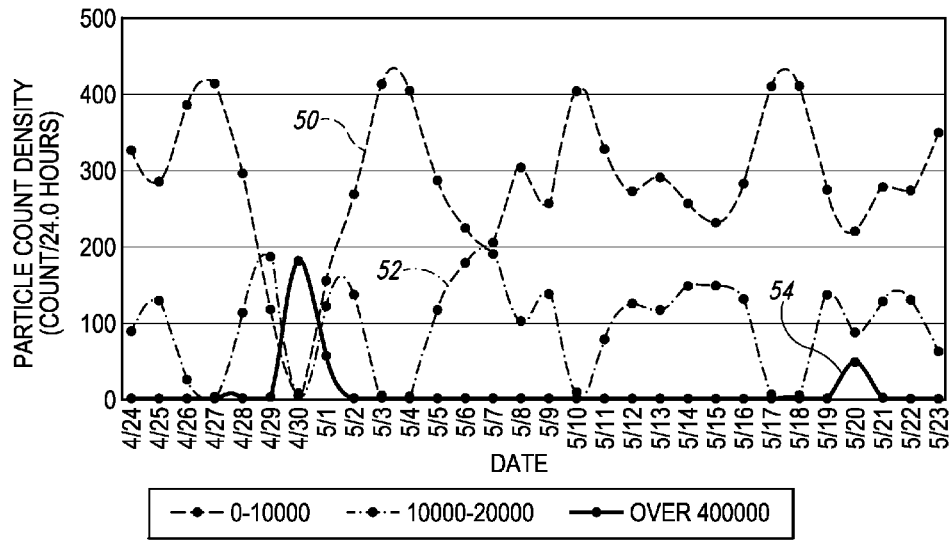
FIG. 6 a plot of the binning process of FIG. 5 illustrating predictive trends that may be observed in the binned airborne particle count data.
Figure 7:
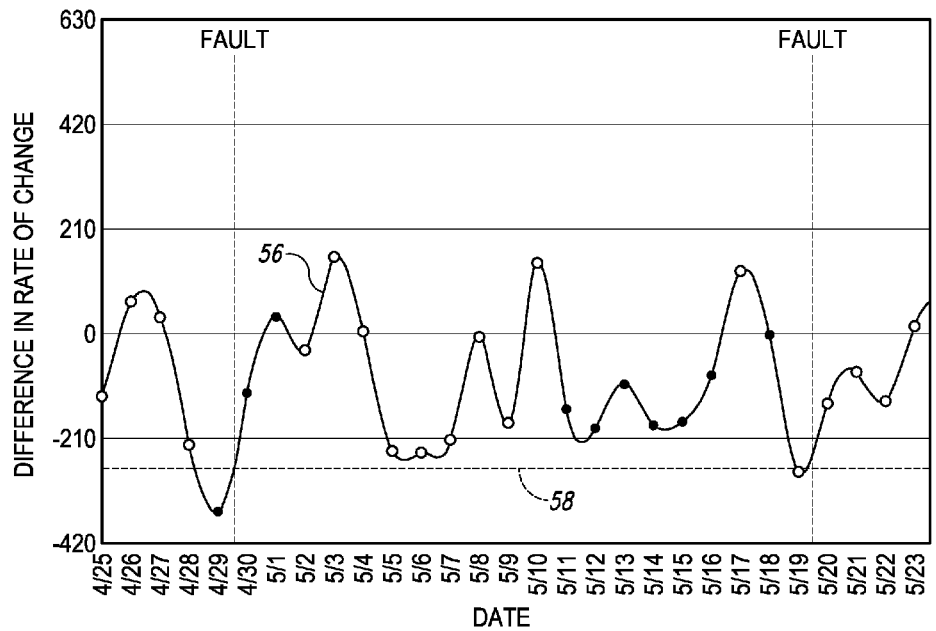
FIG. 7 is a manipulation of the binned airborne particle count data that may be utilized to predict an elevated airborne particle count within the cleanroom environment.

FIG. 2 is a flowchart depicting a method 100, according to the present disclosure, of determining predictive limits to predict and/or detect a fault condition for a time-based complex data set. FIGS. 3-4 are examples of two different portions of a complex data set, in the form of airborne particle count data 40, that may be utilized with method 100 of FIG. 2, while FIGS. 5-7 are examples of data manipulations of airborne particle count data 40 that may be performed as part of methods 100.

In the examples of FIGS. 3-4, the complex data set is in the form of airborne particle count data 40 from a cleanroom environment that is measured as a function of time. FIGS.

3-4 also illustrate a control limit 42 for airborne particle count data 40. When airborne particle count data 40 is above control limit 42, the cleanroom environment is experiencing a fault condition. FIG. 3 illustrates airborne particle count data 40 during a first fault condition that began at a first time 44, while FIG. 4 illustrates airborne particle count data 40 during a second fault condition that began at a second time 46. As discussed in more detail herein, such fault conditions may be detrimental to processes that are performed in the cleanroom environment. With this in mind, method 100 of FIG. 2 may be utilized to establish predictive limits that may predict and/or detect the fault condition before it occurs. This may permit an operator of the cleanroom to address, remove, and/or eliminate a particle source from the cleanroom environment prior to the cleanroom environment experiencing the fault condition.

The complex data set of FIGS. 3-4 may be significantly larger than illustrated and/or may include a significant period of time in which airborne particle count data 40 is below control limit 42 prior to the first fault condition illustrated in FIG. 3, between the first fault condition and the second fault condition illustrated in FIG. 4, and/or subsequent to the second fault condition. The complex data set of FIGS. 3-4 also may be referred to herein as a time-based complex data set and may include a plurality of values of a variable (i.e., the particle count) and a corresponding time stamp for each of the values of the variable (i.e., the time at which the particle count was measured). While FIGS. 3-4 illustrate the complex data set in the form of airborne particle count data 40, it is within the scope of the present disclosure that the method of FIG. 2 may be utilized to determine predictive limits for any suitable complex data set.

Methods 100 include selecting an elapsed time at 110, separating a complex data set into a plurality of non-overlapping subsets at 120, and selecting a variable value limit at 130. Methods 100 further include selecting a number of bins for a binning process at 140, dividing the variable value limit by the number of bins at 150, and determining respective bin counts for the bins at 160. Methods 100 also include chronologically plotting the respective bin count for each bin at 170 and selecting a trend from the plotted bins at 180.

Selecting the elapsed time at 110 may include selecting any suitable elapsed time, time period, and/or timeframe to be utilized during the separating at 120. In general, the elapsed time may be selected and/or based, at least in part, on a desired timeframe between prediction of the fault condition and actual occurrence of the fault condition. Stated another way, the selecting at 110 may be utilized to establish a size of the non-overlapping subsets that are generated during the separating at 120, and this size may impact an amount of time that elapses between when a given predictive limit will be reached and the occurrence of the fault condition. Generally, increasing the elapsed time may increase the amount of time between the predictive limit being reached and occurrence of the fault condition; however, increasing the elapsed time also may decrease a sensitivity of the predictive limit to the fault condition. Conversely, decreasing the elapsed time may decrease the amount of time between the predictive limit being reached and occurrence of the fault condition while increasing the sensitivity of the predictive limit to the fault condition.

Generally, it may be desirable to predict the fault condition with enough time to respond to the prediction prior to the actual fault condition, thereby permitting avoidance of the fault condition. In the context of the cleanroom environment, the elapsed time may be selected to be at least 1 hour, at least 2 hours, at least 4 hours, at least 6 hours, at least 9 hours, at least 12 hours, at least 18 hours, and/or at least 24 hours. Additionally or alternatively, the elapsed time also may be selected to be less than 48 hours, less than 42 hours, less than 36 hours, less than 30 hours, less than 27 hours, and/or less than 24 hours. The elapsed time also may be selected to be 12 hours, 18 hours, 24 hours, 30 hours, and/or 36 hours.

Separating the complex data set into the plurality of non-overlapping subsets at 120 may include separating and/or dividing the complex data set into the plurality of non-overlapping subsets based upon the elapsed time that was selected during the selecting at 110. As an example, an initial non-overlapping subset may begin at an initial time for the complex data set and may extend over a timeframe that corresponds to, or equals, the elapsed time. As another example, a subsequent non-overlapping subset may begin immediately after the initial non-overlapping data set and also may extend over a timeframe that corresponds to, or equals, the elapsed time. Thus, each of the plurality of non-overlapping subsets may extend over a respective timeframe that may correspond to, or equal, the elapsed time. In addition, each of the plurality of non-overlapping subsets may be (immediately) adjacent to another non-overlapping subset such that the entire (or nearly the entire) complex data set is separated into the plurality of non-overlapping subsets. An example of an elapsed time for the non-overlapping subsets is illustrated in FIGS. 3-4 at 48.

Selecting the variable value limit, V, at 130 may include selecting any suitable variable value limit above which the fault condition is predicted. Generally, the variable value limit may be selected based upon, or may even be, a control limit for the complex data set (as illustrated in FIGS. 3-4 at 42) and/or may be based upon a value of the variable that corresponds to the fault condition (i.e., airborne particle count data 40 being above control limit 42 in FIGS. 3-4). However, other variable value limits may be utilized. As an example, and in order to predict the fault condition even earlier, the variable value limit may be selected to be less than (or a percentage of) the control limit. Examples of the percentage of the control limit include percentages of 90%, 80%, 70%, 60%, 50%, less than 90%, less than 80%, less than 70%, less than 60%, or less than 50%.

Selecting the number, N, of bins for the binning process at 140 may include selecting any suitable number of bins for a binning process that may be utilized to simplify, manipulate, and/or otherwise characterize the complex data set during the dividing at 150, the determining at 160, the plotting at 170, and/or the selecting at 180. The number of bins may be selected based upon any suitable criteria, including prior knowledge of the complex data set and/or prior analysis of the complex data set. Additionally or alternatively, the number of bins may be optimized to improve prediction of the fault condition utilizing the predictive limits obtained by performing methods 100. In the example of FIGS. 3-7, the number of bins is selected to be 40; however, it is within the scope of the present disclosure that the number of bins may be at least 2, at least 4, at least 5, at least 10, at least 15, at least 20, at least 30, and/or at least 40. Additionally or alternatively, the number of bins also may be less than 100, less than 90, less than 80, less than 70, less than 60, less than 50, and/or less than 40.

Dividing the variable value limit by the number of bins at 150 may include dividing to obtain a corresponding variable value range, R, for each of the bins. In the example of FIGS. 3-4, the variable value limit, V, is 400,000 particles per cubic meter and the number of bins is selected to be 40. Under these conditions, the variable value range for each bin, R, is 10,000. R may be generally described by R=V/N. Correspondingly, if the bins are numbered 1 to N, the Nth bin may begin at a variable value of (N−1)*R and may end at a variable value of N*R.

Determining respective bin counts for the bins at 160 may include determining the respective bin counts for each non-overlapping subset that was established during the separating at 120. As an example, the determining at 160 may include counting a number of times that the value of the variable within a given non-overlapping subset is within a given bin (i.e., between (N−1)*R and N*R for the Nth bin). Stated another way, each variable value in each non-overlapping subset may be allocated to a specific bin, with the specific bin being selected such that the variable value falls between a lower limit (i.e., (N−1)*R) and an upper limit (i.e., N*R) for the specific bin and the bin count for each bin being equal to a number of times that the variable value is allocated to the bin.

Chronologically plotting the respective bin count for each bin at 170 may include plotting to produce a plurality of chronological bin plots. This is illustrated in FIG. 5. Therein, each of 40 bins has a range, R, of 10,000 particles per cubic meter and each non-overlapping subset has an elapsed time of 24 hours. Thus, FIG. 5 plots one point per day for each of the 40 bins. In FIG. 5, a first bin 50 plots a number of times that the airborne particle count data is between 0 and 10,000 particles per cubic meter (illustrated as a dashed line); a second bin 52 plots a number of times that the airborne particle count data is between 10,000 and 20,000 particles per cubic meter (illustrated as a dash-dot line); and an Nth bin, Bin N, plots a number of times that the airborne particle count data is between (N−1)*10,000 and N*10,000 particles per cubic meter.

The number of times that the airborne particle count data is above 400,000 particles per cubic meter (i.e., above the control limit) is illustrated as a solid line at 54 to indicate the occurrence of the fault condition. As may be seen from FIG. 5, the first fault condition occurred on 4/30, and the second fault condition occurred on 5/20. As discussed, method 100 may be utilized to establish and/or determine predictive limits for the complex data set of FIGS. 3-4 that may be utilized to predict occurrence of the fault conditions prior to actual occurrence of the fault conditions.

As illustrated in FIG. 5, first bin 50 and second bin 52 exhibit the greatest variation with time. FIG. 6 plots first bin 50, second bin 52, and the number of times 54 that the airborne particle count is above 400,000.

Selecting the trend from the plotted bins at 180 may include analyzing and/or observing the plurality of chronological bin plots to establish and/or determine a trend in the plurality of chronological bin plots that is predictive of the fault condition. As illustrated in FIG. 6, prior to occurrence of both the first fault condition (on 4/30) and the second fault condition (on 5/20), first bin 50 increases sharply, going through a local maximum, before decreasing sharply. Conversely, second bin 52 decreases sharply, going through a local minimum, before increasing sharply. This observed behavior of first bin 50 and second bin 52 may be analyzed in several ways in order to determine whether or not it is predictive of the fault conditions.

As an example, a magnitude of first bin 50 as a function of time may be analyzed; however, in the case of FIG. 6, no systematic and/or predictive behavior was observed, since at least the 5/3 and the 5/4 data points show similar magnitudes but no immediately subsequent fault condition. As another example, a magnitude of second bin 52 as a function of time also may be analyzed; however, in the case of FIG. 6, no systematic and/or predictive behavior was observed since at least the 5/3 and the 5/4 data points show similar magnitudes but no immediately subsequent fault condition. As yet another example, a rate of change of first bin 50 and/or of second bin 52 may be analyzed. However, once again, no systematic and/or predictive behavior was observed.

As another example a difference 56 in the rate of change of first bin 50 and the rate of change of second bin 52 may be analyzed. This is illustrated in FIG. 7. As shown in FIG. 7, difference 56 was consistently below a threshold value 58 immediately prior to the first fault condition and the second fault condition and consistently above threshold value 58 at other times. Thus, difference 56 may be utilized to predict the fault conditions. As an example, when difference 56 is below threshold value 58, the fault condition is predicted. However, when difference 56 is above threshold value 58 (or within a predetermined threshold difference range that includes all values of difference 56 that are greater than threshold value 58), the fault condition is not predicted.

Figure 8:
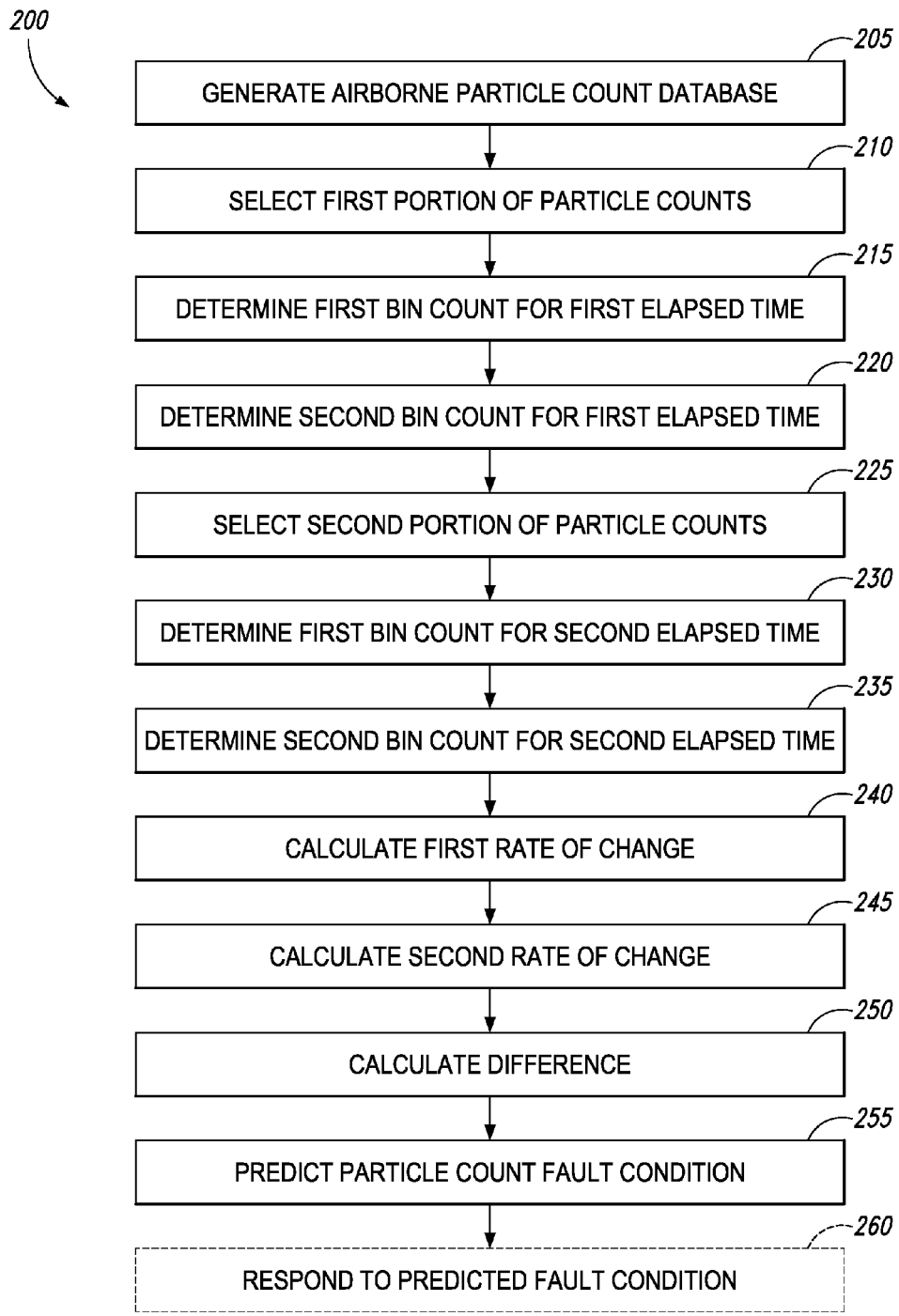
FIG. 8 is a flowchart depicting methods, according to the present disclosure, of analyzing airborne particle count data from a cleanroom environment to predict a particle fault condition within the cleanroom environment.

FIG. 8 is a flowchart depicting methods 200, according to the present disclosure, of analyzing airborne particle count data from a cleanroom environment to predict a particle fault condition within the cleanroom environment. Methods 200 include generating an airborne particle count data repository that includes particle counts and a corresponding time stamp for each of the particle counts at 205, selecting a first portion of the particle counts at 210, determining a first bin count for a first elapsed time at 215, and determining a second bin count for the first elapsed time at 220. Methods 200 further include selecting a second portion of the particle counts at 225, determining a first bin count for a second elapsed time at 230, and determining a second bin count for the second elapsed time at 235. Methods 200 also include calculating a first rate of change at 240, calculating a second rate of change at 245, calculating a difference between the first rate of change and the second rate of change at 250, and predicting a particle count fault condition at 255. Methods 200 also may include responding to the predicted particle count fault condition at 260.

Generating the airborne particle count data repository that includes particle counts and the corresponding time stamp for each of the particle counts at 205 may include generating the airborne particle count data repository in any suitable manner. As an example, the generating at 205 may include collecting and/or detecting particle counts within the cleanroom environment with a distributed cleanroom particle monitoring system, such as system 30 of FIG. 1.

It is within the scope of the present disclosure that the generating at 205 may include continuously, or at least substantially continuously, generating the airborne particle count data repository during a remainder of the method. As an example, the generating at 205 may include adding a subsequent particle count to the airborne particle count data repository with at least a threshold particle count frequency during a remainder of the method. Examples of the threshold particle count frequency are disclosed herein.

For each particle count that is added to the airborne particle count data repository, the generating at 205 may include determining a particle count within an air volume of the cleanroom environment. The particle count may be determined with a detection node of the distributed cleanroom particle count monitoring system. The generating at 205 further may include transmitting a particle count signal that is indicative of the particle count. The generating at 205 also may include receiving the particle count signal. The particle count signal may be received by a receiver of a data analysis system, such as receiver 62 of data analysis system 60 of FIG. 1. The generating at 205 also may include determining the particle count based upon the particle count signal. This may include determining the particle count with the data analysis system. The generating at 205 further may include storing the particle count and a corresponding time stamp for the particle count to generate the airborne particle count data repository. The particle count and the time stamp may be stored on a data storage device, such as data storage device 64 of FIG. 1.

When the generating at 205 includes generating with the distributed cleanroom particle count monitoring system, the distributed cleanroom particle count monitoring system may include a plurality of detection nodes that may be spaced apart within the cleanroom environment. Each of the plurality of detection nodes may be configured to determine a respective particle count proximal thereto. This may include determining the respective particle count within a respective air volume of a respective node location within the cleanroom environment. Under these conditions, the airborne particle count data repository may include respective particle counts from each of the plurality of detection nodes. In addition, the airborne particle count data repository also may include a respective measurement location (or node location) for each of the particle counts, and the respective measurement location may be indicative of the respective node location where a respective particle count was measured within the cleanroom environment. When the airborne particle count data repository is generated with the plurality of detection nodes, the predicting at 255 further may include predicting which node location within the cleanroom environment will experience the predicted particle count fault condition.

Selecting the first portion of the particle counts at 210 may include selecting the first portion of the particle counts from the airborne particle count data repository. The selecting at 210 may be performed subsequent to the generating at 205 being performed for the first elapsed time, and the first portion of the particle counts may include particle counts with a corresponding time stamp that is during the first elapsed time. As an example, the selecting at 210 may include selecting a fraction and/or subset of the particle counts that was generated during the first elapsed time, that was determined during the first elapsed time, and/or that was stored within the airborne particle count data repository during the first elapsed time.

Determining the first bin count for the first elapsed time at 215 may include determining a number of the first portion of the particle counts that is between a first lower particle count and a first upper particle count. The first lower particle count may be less than the first upper particle count. As an example, the determining at 215 may include counting a number of times that the first portion of the particle counts is between the first lower particle count and the first upper particle count and/or counting a number of times that the first portion of the particle counts is greater than the first lower particle count but less than the first upper particle count.

Determining the second bin count for the first elapsed time at 220 may include determining a number of the first portion of the particle counts that is between a second lower particle count and a second upper particle count. The second lower particle count may be greater than or equal to the first upper particle count. The second upper particle count may be greater than the second lower particle count. As an example, the determining at 220 may include counting a number of times that the first portion of the particle counts is between the second lower particle count and the second upper particle count and/or counting a number of times that the first portion of the particle counts is greater than the second lower particle count but less than the second upper particle count.

The first lower particle count, the first upper particle count, the second lower particle count, and the second upper particle count may be determined and/or established in any suitable manner. As an example, the particle counts may be predetermined based upon prior analysis of a portion of the airborne particle count data repository. As another example, the particle counts may be predetermined based upon prior analysis of airborne particle count data that was collected within the cleanroom. As yet another example, the particle counts may be predetermined by performing methods 100 to select which bin(s) are predictive of the particle count fault condition.

As a more specific example, the cleanroom environment may have a particle count upper control limit; and the first lower particle count, the first upper particle count, the second lower particle count, and the second upper particle count may be based, at least in part, on the upper control limit. As an example, the first lower particle count, the first upper particle count, the second lower particle count, and the second upper particle count may be determined by dividing the particle count upper control limit into a plurality of bins to determine which of the plurality of bins is predictive of the particle count fault condition, as discussed herein with reference to methods 100. As another more specific example, the first lower particle count may be 0, the first upper particle count may be 10,000, the second lower particle count may be 10,000, and the second upper particle count may be 20,000.

Selecting the second portion of the particle counts at 225 may include selecting the second portion of the particle counts from the airborne particle count data repository. The selecting at 225 may be performed subsequent to the generating at 205 being performed for the second elapsed time, and the second portion of the particle counts may include particle counts with a corresponding time stamp that is during the second elapsed time. As an example, the selecting at 225 may include selecting a fraction and/or subset of the particle counts that was generated during the second elapsed time, that was determined during the second elapsed time, and/or that was stored within the airborne particle count data repository during the second elapsed time.

The second elapsed time may be (immediately) after the first elapsed time. As an example, the first elapsed time may extend between a first time and a second time that is greater than the first time. The second elapsed time may extend between the second time and a third time that is greater than the second time. The first elapsed time may be (at least substantially) equal to the second elapsed time. Examples of the first elapsed time and the second elapsed time are disclosed herein with reference to the elapsed time of methods 100.

Determining the first bin count for the second elapsed time at 230 may include determining a number of the second portion of the particle counts that is between the first lower particle count and the first upper particle count. As an example, the determining at 230 may include counting a number of times that the second portion of the particle counts is between the first lower particle count and the first upper particle count and/or counting a number of times that the second portion of the particle counts is greater than the first lower particle count but less than the first upper particle count.

Determining the second bin count for the second elapsed time at 235 may include determining a number of the second portion of the particle counts that is between the second lower particle count and the second upper particle count. As an example, the determining at 235 may include counting a number of times that the second portion of the particle counts is between the second lower particle count and the second upper particle count and/or counting a number of times that the second portion of the particle counts is greater than the second lower particle count but less than the second upper particle count.

Calculating the first rate of change at 240 may include calculating a first rate of change between the first bin count for (or as determined at) the first elapsed time and the first bin count for (or as determined at) the second elapsed time. As an example, the calculating at 240 may include calculating a first difference by subtracting the first bin count at the first elapsed time from the first bin count at the second elapsed time and dividing the first difference by the second elapsed time.

Calculating the second rate of change at 245 may include calculating a second rate of change between the second bin count for (or as determined at) the first elapsed time and the second bin count for (or as determined at) the second elapsed time. As an example, the calculating at 245 may include calculating a second difference by subtracting the second bin count at the first elapsed time from the second bin count at the second elapsed time and dividing the second difference by the second elapsed time.

Calculating the difference between the first rate of change and the second rate of change at 250 may be accomplished in any suitable manner. As an example, the calculating at 250 may include subtracting the second rate of change from the first rate of change.

Predicting the particle count fault condition at 255 may include predicting that the particle count fault condition will be experienced within the cleanroom environment at a future time. The predicting at 255 may be based, at least in part, on the first rate of change and the second rate of change. As an example, the predicting at 255 may be performed responsive to the difference between the first rate of change and the second rate of change being outside a predetermined threshold difference range, being greater than an upper threshold value, and/or being less than a lower threshold value. The predetermined threshold difference range may be predetermined based upon prior analysis of a portion of the airborne particle count data repository. Additionally or alternatively, the predetermined threshold difference range also may be predetermined based upon prior analysis of airborne particle count data that was collected within the cleanroom environment and/or within another cleanroom environment. As yet another example, the predetermined threshold difference range may be predetermined utilizing methods 100, which are discussed in more detail herein.

Responding to the predicted particle count fault condition at 260 may include responding in any suitable manner and/or may include performing any suitable action. As an example, the responding at 260 may include generating a notification to a user. The notification may be indicative of the predicted particle count fault condition. Examples of the notification include generating an alert. Generating the alert may include sounding an alarm, actuating a buzzer, powering a light, displaying a color-coded display, displaying a graphical display, and/or displaying a numeric display. Each of these notifications may be indicative of and/or may notify the user of the predicted particle count fault condition.

As another example, the responding at 260 also may include replacing one or more filters within the cleanroom environment. As yet another example, the responding at 260 may include performing additional particle testing within the clean room environment. As another example, the responding at 260 may include evaluating the cleanroom environment to determine a source of the predicted particle count fault condition.

It is within the scope of the present disclosure that methods 200 may be performed and/or repeated any suitable number of times to determine the first and second bin counts, calculate the first and second rates of change, and/or predict the particle count fault condition for any suitable elapsed time period. As an example, methods 200 may include repeating (or performing) the generating at 205 for a subsequent elapsed time that is after the second elapsed time. As another example, methods 200 also may include selecting a subsequent portion of the particle counts from the airborne particle count data repository. The subsequent portion of the particle counts may include particle counts with a corresponding time stamp that is during the subsequent elapsed time.

As yet another example, methods 200 may include determining a first bin count for the subsequent elapsed time and determining a second bin count for the subsequent elapsed time. As another example, methods 200 may include calculating a subsequent rate of change for the first bin count between a prior elapsed time and the subsequent elapsed time and also calculating a subsequent rate of change for the second bin count between the prior elapsed time and the subsequent elapsed time.

As yet another example, methods 200 further may include calculating a difference between the subsequent rate of change for the first bin count and the subsequent rate of change for the second bin count. As another example, methods 200 may include predicting the particle count fault condition within the cleanroom environment responsive to the difference between the subsequent rate of change for the first bin count and the subsequent rate of change for the second bin count being outside the predetermined threshold difference range.

Illustrative, non-exclusive examples of inventive subject matter according to the present disclosure are described in the following enumerated paragraphs:

A1. A method of analyzing airborne particle count data from a cleanroom environment to predict a particle count fault condition within the cleanroom environment, the method comprising:

generating an airborne particle count data repository that includes particle counts within the cleanroom environment and a corresponding time stamp for each of the particle counts;

subsequent to performing the generating for a first elapsed time, optionally selecting a first portion of the particle counts from the airborne particle count data repository that includes particle counts with a corresponding time stamp that is during the first elapsed time;

optionally determining a first bin count for the first elapsed time by determining a number of the first portion of the particle counts that is between a first lower particle count and a first upper particle count, wherein the first upper particle count is greater than the first lower particle count;

optionally determining a second bin count for the first elapsed time by determining a number of the first portion of the particle counts that is between a second lower particle count and a second upper particle count, wherein the second lower particle count is greater than or equal to the first upper particle count, and further wherein the second upper particle count is greater than the second lower particle count;

subsequent to performing the generating for a second elapsed time that is subsequent to the first elapsed time, optionally selecting a second portion of the particle counts from the airborne particle count data repository that includes particle counts with a corresponding time stamp that is during the second elapsed time;

optionally determining a first bin count for the second elapsed time by determining a number of the second portion of the particle counts that is between the first lower particle count and the first upper particle count;

optionally determining a second bin count for the second elapsed time by determining a number of the second portion of the particle counts that is between the second lower particle count and the second upper particle count;

optionally calculating a first rate of change of a first bin count of the airborne particle count data repository, wherein the first rate of change includes a rate of change between the first bin count for the first elapsed time and the first bin count for the second elapsed time;

optionally calculating a second rate of change of a second bin count of the airborne particle count data repository, wherein the second rate of change includes a rate of change between the second bin count for the first elapsed time and the second bin count for the second elapsed time;

calculating a difference between the first rate of change and the second rate of change; and responsive to the difference between the first rate of change and the second rate of change being outside a predetermined threshold difference range, predicting the particle count fault condition within the cleanroom environment.

A2. The method of paragraph A1, wherein the generating includes continuously adding, during a remainder of the method, a subsequent particle count to the airborne particle count data repository with at least a threshold particle count frequency.

A3. The method of any of paragraphs A1-A2, wherein the generating includes repeatedly:

(i) determining a particle count within an air volume of the cleanroom environment with a detection node of a distributed cleanroom particle count monitoring system;

(ii) transmitting a particle count signal that is indicative of the particle count;

(iii) receiving the particle count signal with a data analysis system;

(iv) determining, with the data analysis system, the particle count based upon the particle count signal; and (v) storing the particle count and the corresponding time stamp for the particle count on a data storage device to generate the airborne particle count data repository.

A4. The method of any of paragraphs A1-A3, wherein the generating includes generating with a/the distributed cleanroom particle count monitoring system that includes a plurality of detection nodes, wherein each of the plurality of detection nodes is configured to determine a respective particle count within a respective air volume of a respective node location within the cleanroom environment, and further wherein the airborne particle count data repository includes respective particle counts from each of the plurality of detection nodes.

A5. The method of paragraph A4, wherein the airborne particle count data repository further includes a respective measurement location for each of the particle counts, wherein the respective measurement location is indicative of the respective node location within the cleanroom environment where the particle count was measured.

A6. The method of paragraphs A5, wherein the predicting the particle count fault condition further includes predicting which node location within the cleanroom environment will experience the predicted particle count fault condition.

A7. The method of any of paragraphs A1-A6, wherein the selecting the first portion of the particle counts from the airborne particle count data repository includes selecting a fraction of the particle counts that was generated during the first elapsed time.

A8. The method of any of paragraphs A1-A7, wherein the selecting the second portion of the particle counts from the airborne particle count data repository includes selecting a fraction of the particle counts that was generated during the second elapsed time.

A9. The method of any of paragraphs A1-A8, wherein the first elapsed time extends between a first time and a second time that is greater than the first time, and further wherein the second elapsed time extends between the second time and a third time that is greater than the second time.

A10. The method of any of paragraphs A1-A9, wherein the first elapsed time is (at least substantially) equal to the second elapsed time.

A11. The method of any of paragraphs A1-A10, wherein at least one of the first elapsed time and the second elapsed time is at least one of:

(i) at least 1 hour, at least 2 hours, at least 4 hours, at least 6 hours, at least 9 hours, at least 12 hours, at least 18 hours, or at least 24 hours;

(ii) less than 48 hours, less than 42 hours, less than 36 hours, less than 30 hours, less than 27 hours, or less than 24 hours; and (iii) 12 hours, 18 hours, 24 hours, 30 hours, or 36 hours.

A12. The method of any of paragraphs A1-A11, wherein the determining the first bin count for the first elapsed time includes counting a number of times that the first portion of the particle counts is between the first lower particle count and the first upper particle count.

A13. The method of any of paragraphs A1-A12, wherein the determining the second bin count for the first elapsed time includes counting a number of times that the first portion of the particle counts is between the second lower particle count and the second upper particle count.

A14. The method of any of paragraphs A1-A13, wherein the determining the first bin count for the second elapsed time includes counting a number of times that the second portion of the particle counts is between the first lower particle count and the first upper particle count.

A15. The method of any of paragraphs A1-A14, wherein the determining the second bin count for the second elapsed time includes counting a number of times that the second portion of the particle counts is between the second lower particle count and the second upper particle count.

A16. The method of any of paragraphs A1-A15, wherein the first lower particle count, the first upper particle count, the second lower particle count, and the second upper particle count are predetermined based upon prior analysis of at least one of (i) a portion of the airborne particle count data repository and (ii) airborne particle count data that was collected within the cleanroom environment.

A17. The method of any of paragraphs A1-A16, wherein the cleanroom environment has a particle count upper control limit, and further wherein the first lower particle count, the first upper particle count, the second lower particle count, and the second upper particle count are based, at least in part, on the upper control limit.

A18. The method of any of paragraphs A1-A17, wherein the cleanroom environment has a/the particle count upper control limit, and further wherein the first lower particle count, the first upper particle count, the second lower particle count, and the second upper particle count are determined by dividing the particle count upper control limit into a plurality of bins and analyzing the plurality of bins to determine which of the plurality of bins is predictive of the particle count fault condition.

A19. The method of any of paragraphs A1-A18, wherein the first lower particle count is zero and the first upper particle count is 10,000.

A20. The method of any of paragraphs A1-A19, wherein the second lower particle count is 10,000 and the second upper particle count is 20,000.

A21. The method of any of paragraphs A1-A20, wherein the calculating the first rate of change between the first bin count for the first elapsed time and the first bin count for the second elapsed time includes subtracting the first bin count for the first elapsed time from the first bin count for the second elapsed time to calculate a first difference and dividing the first difference by the second elapsed time.

A22. The method of any of paragraphs A1-A21, wherein the calculating the second rate of change between the second bin count for the first elapsed time and the second bin count for the second elapsed time includes subtracting the second bin count for the first elapsed time from the second bin count for the second elapsed time to calculate a second difference and dividing the second difference by the second elapsed time.

A23. The method of any of paragraphs A1-A22, wherein the calculating the difference between the first rate of change and the second rate of change includes subtracting the second rate of change from the first rate of change.

A24. The method of any of paragraphs A1-A23, wherein the predicting the particle count fault condition includes predicting that the cleanroom environment will experience the particle count fault condition at a future time.

A25. The method of any of paragraphs A1-A24, wherein the predicting the particle count fault condition includes predicting based, at least in part, on the difference between the first rate of change and the second rate of change.

A26. The method of any of paragraphs A1-A25, wherein the predetermined threshold difference range is predetermined based upon prior analysis of at least one of (i) a/the portion of the airborne particle count data repository and (ii) airborne particle count data that was collected within the cleanroom environment.

A27. The method of any of paragraphs A1-A26, wherein the method further includes responding to a predicted particle count fault condition.

A28. The method of paragraph A27, wherein the responding includes generating the notification to a user that is indicative of the predicted particle count fault condition.

A29. The method of paragraph A28, wherein the generating a notification includes at least one of generating an alert, sounding an alarm, actuating a buzzer, powering a light, displaying a color-coded display, displaying a graphical display, and displaying a numeric display that is indicative of the predicted particle count fault condition.

A30. The method of any of paragraphs A27-A29, wherein the responding includes at least one of (i) replacing an air filter within the cleanroom environment, (ii) performing additional particle testing within the cleanroom environment, and (iii) evaluating the cleanroom environment to determine a source of the predicted particle count fault condition.

A31. The method of any of paragraphs A1-A30, wherein the method further includes:

(i) performing the generating for a subsequent elapsed time;

(ii) selecting a subsequent portion of the particle counts from the airborne particle count data repository that includes particle counts with a corresponding time stamp that is during the subsequent elapsed time;

(iii) determining a first bin count for the subsequent elapsed time;

(iv) determining a second bin count for the subsequent elapsed time;

(v) calculating a subsequent rate of change for the first bin count between a prior elapsed time and the subsequent elapsed time;

(vi) calculating a subsequent rate of change for the second bin count between the prior elapsed time and the subsequent elapsed time;

(vii) calculating a difference between the subsequent rate of change for the first bin count and the subsequent rate of change for the second bin count; and (viii) responsive to the difference between the subsequent rate of change for the first bin count and the subsequent rate of change for the second bin count being outside the predetermined threshold difference range, predicting the particle count fault condition within the cleanroom environment.

B1. A method of determining predictive limits to predict a fault condition for a time-based complex data set that includes values of a variable and a corresponding time stamp for each of the values of the variable, the method comprising:

selecting an elapsed time, wherein the elapsed time is based, at least in part, on a desired timeframe between prediction of the fault condition and actual occurrence of the fault condition;

separating the complex data set into a plurality of non-overlapping subsets, wherein each of the plurality of non-overlapping subsets extends over a respective timeframe that corresponds to the selected elapsed time;

selecting a variable value limit for a binning process, wherein the variable value limit is based, at least in part, on a value of the variable that corresponds to the fault condition;

selecting a number of bins for the binning process;

dividing the variable value limit by the number of bins to obtain a corresponding variable value range (R) for each bin in the number of bins, wherein the number of bins is numbered from 1 to N, and further wherein the Nth bin extends from $(N-1)*R$ to $N*R$;

determining a respective bin count for each bin in the number of bins within each non-overlapping subset by counting a number of times that the value of the variable within a given non-overlapping subset is within a given bin;

chronologically plotting the respective bin count for each bin in the number of bins to produce a plurality of chronological bin plots; and selecting a trend in one or more of the plurality of chronological bin plots that is predictive of the fault condition.

C1. A distributed cleanroom particle count monitoring system, comprising:

a plurality of detection nodes, wherein the plurality of detection nodes is spaced-apart within a cleanroom environment at a plurality of respective node locations, and further wherein each of the plurality of detection nodes includes:

(i) a particle sensor configured to determine a particle count within a respective air volume of a respective node location; and (ii) a transmitter configured to generate a particle count signal indicative of the particle count within the respective air volume;

a receiver configured to receive a plurality of respective particle count signals from the plurality of detection nodes;

a data analysis system programmed to analyze the plurality of respective particle count signals to determine a plurality of respective particle counts; and a data storage device configured to store the plurality of respective particle counts.

C2. The system of paragraph C1, wherein the data storage device is further configured to store a respective one of the plurality of the respective node locations for each of the plurality of respective particle counts.

C3. The system of any of paragraphs C1-C2, wherein the data storage device is further configured to store a time stamp for each of the plurality of respective particle counts.

C4. The system of any of paragraphs C1-C3, wherein each of the plurality of detection nodes is configured to continuously determine the particle count within the respective air volume.

C5. The system of any of paragraphs C1-C4, wherein each of the plurality of detection nodes is configured to determine the particle count within the respective air volume with at least a threshold particle count frequency, optionally wherein the threshold particle count frequency is at least once per 1 second interval, at least once per 5 second interval, at least once per 10 second interval, at least once per 30 second interval, at least once per 1 minute interval, at least once per 5 minute interval, at least once per 10 minute interval, at least once per 15 minute interval, at least once per 30 minute interval, at least once per 1 hour interval, at least once per 2 hour interval, or at least once per 4 hour interval.

C6. The system of any of paragraphs C1-05, wherein the plurality of detection nodes is spaced apart in a two-dimensional detection node array.

C7. The system of any of paragraphs C1-C6, wherein each of the plurality of detection nodes is spaced apart from a nearest other of the plurality of detection nodes by at least one of:

(i) at least 1 meter, at least 2.5 meters, at least 5 meters, at least 7.5 meters, or at least 10 meters; and (ii) less than 30 meters, less than 25 meters, less than 20 meters, less than 15 meters, less than 10 meters, or less than 5 meters.

C8. The system of any of paragraphs C1-C7, wherein the transmitter includes at least one of a wireless transmitter configured to generate a wireless particle count signal and a wired transmitter configured to generate a wired particle count signal.

C9. The system of any of paragraphs C1-C8, wherein the receiver includes at least one of a wireless receiver configured to receive a/the wireless particle count signal and a wired receiver configured to receive a/the wired particle count signal.

C10. The system of any of paragraphs C1-C9, wherein the system further includes a notification system configured to notify a user of a particle count fault condition that is predicted by analysis of the plurality of respective particle counts, wherein the data analysis system is configured to generate a fault indication signal responsive to the data analysis system predicting the particle count fault condition, and further wherein the notification system is configured to receive the fault indication signal and to, responsive to receipt of the fault indication signal, notify the user of the predicted particle count fault condition.

C11. The system of paragraph C10, wherein the notification system includes at least one of an alarm, a buzzer, a light, a color-coded display, a graphical display, and an alphanumeric display that is indicative of the particle count fault condition.

C12. The system of any of paragraphs C1-C11, wherein the data analysis system is programmed to predict a/the particle count fault condition based, at least in part, on the plurality of respective particle counts.

C13. The system of any of paragraphs C1-C12, wherein the data analysis system is programmed to perform the method of any of paragraphs A1-B1.

D1. A data analysis system programmed to perform the method of any of paragraphs A1-B1.

D2. The system of paragraph D1, wherein the data analysis system includes at least one of:

(i) a communications framework;
(ii) a processor unit;
(iii) a data storage device;
(iv) memory;
(v) persistent storage;
(vi) a communications unit;
(vii) an input/output unit;
(viii) a display;
(ix) a storage device;
(x) computer readable media;
(xi) computer readable storage media; and
(xii) computer readable signal media.

D3. The system of any of paragraphs D1-D2, wherein the data analysis system is programmed to execute program code.

D4. The system of any of paragraphs D1-D3, wherein the data analysis system includes at least one of an electronic controller, a dedicated computer, a special-purpose computer, and a personal computer.

D5. Computer readable storage media including computer-executable instructions that, when executed, direct a data analysis system to perform the method of any of paragraphs A1-B1.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus. As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

Aspects of the present disclosure may be embodied as a computer method, computer system, or computer program product. Accordingly, aspects of the present disclosure may take the form of an entirely hardware embodiment, an entirely software embodiment (including firmware, resident software, micro-code, and the like), or an embodiment combining software and hardware aspects, all of which may generally be referred to herein as a "circuit," "module," or "system." Furthermore, aspects of the present disclosure may take the form of a computer program product embodied in a computer-readable medium (or media) having computer readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the present invention may be written in one or any combination of programming languages, including an object-oriented programming language such as Java, Smalltalk, C++, and/or the like, and conventional procedural programming languages, such as the C programming language. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of the present invention are described herein with reference to flowchart illustrations and/or block diagrams of methods, apparatuses, systems, and/or computer program products according to aspects of the present disclosure. Each block and/or combination of blocks in a flowchart and/or block diagram may be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions also can be stored in a computer-readable medium that can direct a computer, other programmable data processing apparatus, and/or other device to function in a particular manner, such that the instructions stored in the computer-readable medium produce an article of manufacture including instructions which implement the function/act specified in the flowchart and/or block diagram block or blocks.

The computer program instructions also can be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the flowchart and/or block diagram block or blocks.

Any flowchart and/or block diagram in the drawings is intended to illustrate the architecture, functionality, and/or operation of possible implementations of systems, methods, and computer program products according to aspects of the present disclosure. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

The invention claimed is:

1. A method of analyzing airborne particle count data from a cleanroom environment to predict and respond to a particle count fault condition within the cleanroom environment, the method comprising:

generating an airborne particle count data repository that includes particle counts within the cleanroom environment and a corresponding time stamp for each of the particle counts, wherein the generating includes generating with a distributed cleanroom particle count monitoring system that includes a plurality of detection nodes, and further wherein the airborne particle count data repository includes respective particle counts for each of the plurality of detection nodes;

calculating, with a data analysis system of the distributed cleanroom particle count system, a difference between a first rate of change of a first bin count of the airborne particle count data repository and a second rate of change of a second bin count of the airborne particle count data repository;

responsive to the difference between the first rate of change of the first bin count of the airborne particle count data repository and the second rate of change of the second bin count of the airborne particle count data repository being outside a predetermined threshold difference range, predicting, with the data analysis system, a predicted particle count fault condition within the cleanroom environment;

responding to the predicted particle count fault condition by replacing an air filter within the cleanroom environment to improve filtering of the cleanroom environment; and performing, with the distributed cleanroom particle count monitoring system, additional particle testing within the cleanroom environment to determine whether the predicted particle count fault condition still will be experienced within the cleanroom environment.

2. The method of claim 1, wherein the generating includes continuously adding, during a remainder of the method, a subsequent particle count to the airborne particle count data repository with at least a threshold particle count frequency.

3. The method of claim 1, wherein the calculating the difference between the first rate of change of the first bin count of the airborne particle count data repository and the second rate of change of the second bin count of the airborne particle count data repository includes subtracting the second rate of change from the first rate of change.

4. The method of claim 1, wherein the predicting the particle count fault condition includes predicting that the cleanroom environment will experience the particle count fault condition at a future time.

5. The method of claim 1, wherein the predetermined threshold difference range is predetermined based upon prior analysis of at least one of (i) a portion of the airborne particle count data repository and (ii) airborne particle count data that was collected within the cleanroom environment.

6. The method of claim 1, wherein the responding further includes at least one of:
(i) generating a notification to a user that is indicative of the predicted particle count fault condition;
(ii) evaluating the cleanroom environment to determine a source of the predicted particle count fault condition.

7. The method of claim 1, further comprising:
subsequent to performing the generating for a first elapsed time, selecting a first portion of the particle counts from the airborne particle count data repository that includes particle counts with a corresponding time stamp that is during the first elapsed time;
determining a first bin count for the first elapsed time by determining a number of the first portion of the particle counts that is between a first lower particle count and a first upper particle count, wherein the first upper particle count is greater than the first lower particle count;
determining a second bin count for the first elapsed time by determining a number of the first portion of the particle counts that is between a second lower particle count and a second upper particle count, wherein the second lower particle count is greater than or equal to the first upper particle count, and further wherein the second upper particle count is greater than the second lower particle count;
subsequent to performing the generating for a second elapsed time that is subsequent to the first elapsed time, selecting a second portion of the particle counts from the airborne particle count data repository that includes particle counts with a corresponding time stamp that is during the second elapsed time;
determining a first bin count for the second elapsed time by determining a number of the second portion of the particle counts that is between the first lower particle count and the first upper particle count; and
determining a second bin count for the second elapsed time by determining a number of the second portion of the particle counts that is between the second lower particle count and the second upper particle count.

8. The method of claim 7, wherein the first elapsed time extends between a first time and a second time that is greater than the first time, wherein the second elapsed time extends between the second time and a third time that is greater than the second time, and further wherein the first elapsed time is at least substantially equal to the second elapsed time.

9. The method of claim 7, wherein the determining the first bin count for the first elapsed time includes counting a number of times that the first portion of the particle counts is between the first lower particle count and the first upper particle count, wherein the determining the second bin count for the first elapsed time includes counting a number of times that the first portion of the particle counts is between the second lower particle count and the second upper particle count, wherein the determining the first bin count for the second elapsed time includes counting a number of times that the second portion of the particle counts is between the first lower particle count and the first upper particle count, and further wherein the determining the second bin count for the second elapsed time includes counting a number of times that the second portion of the particle counts is between the second lower particle count and the second upper particle count.

10. The method of claim 7, wherein the first lower particle count, the first upper particle count, the second lower particle count, and the second upper particle count are predetermined based upon prior analysis of at least one of (i) a portion of the airborne particle count data repository and (ii) airborne particle count data that was collected within the cleanroom environment.

11. The method of claim 7, wherein the cleanroom environment has a particle count upper control limit, and further wherein the first lower particle count, the first upper particle count, the second lower particle count, and the second upper particle count are determined by dividing the particle count upper control limit into a plurality of bins and analyzing the plurality of bins to determine which of the plurality of bins is predictive of the particle count fault condition.

12. The method of claim 7, further comprising:
calculating the first rate of change of the first bin count of the airborne particle count data repository, wherein the first rate of change includes a rate of change between the first bin count for the first elapsed time and the first bin count for the second elapsed time; and calculating the second rate of change of the second bin count of the airborne particle count data repository, wherein the second rate of change includes a rate of change between the second bin count for the first elapsed time and the second bin count for the second elapsed time.

13. The method of claim 12, wherein the calculating the first rate of change includes subtracting the first bin count for the first elapsed time from the first bin count for the second elapsed time to calculate a first difference and dividing the first difference by the second elapsed time, and further wherein the calculating the second rate of change includes subtracting the second bin count for the first elapsed time from the second bin count for the second elapsed time to calculate a second difference and dividing the second difference by the second elapsed time.

14. Computer readable storage media including computer-executable instructions that, when executed, direct a data analysis system to perform the method of claim 1.

15. A distributed cleanroom particle count monitoring system, comprising:
   a plurality of detection nodes, wherein the plurality of detection nodes is spaced-apart within a cleanroom environment at a plurality of respective node locations, and further wherein each of the plurality of detection nodes includes:
      (i) a particle sensor configured to determine a particle count within a respective air volume of a respective node location; and
      (ii) a transmitter configured to generate a particle count signal indicative of the particle count within the respective air volume;
   a receiver configured to receive a plurality of respective particle count signals from the plurality of detection nodes;
   a data analysis system programmed to:
      (i) analyze the plurality of respective particle count signals to determine a plurality of respective particle counts;
      (ii) generate an airborne particle count data repository that includes the plurality of respective particle counts;
      (iii) calculate a difference between a first rate of change of a first bin count of the airborne particle count data repository and a second rate of change of a second bin count of the airborne particle count data repository; and
      (iv) responsive to the difference between the first rate of change and the second rate of change being outside a predetermined threshold difference range, predict a predicted particle count fault condition within the cleanroom environment;
   a data storage device configured to store the plurality of respective particle counts; and
   a notification system configured to notify a user of a particle count fault condition that is predicted by analysis of the plurality of respective particle counts, wherein the data analysis system is configured to generate a fault indication signal responsive to the data analysis system predicting the particle count fault condition, and further wherein the notification system is configured to receive the fault indication signal and to, responsive to receipt of the fault indication signal, notify the user of the predicted particle count fault condition.

16. The system of claim 15, wherein the data storage device is further configured to store a respective one of the plurality of respective node locations for each of the plurality of respective particle counts, and further wherein the data storage device is configured to store a time stamp for each of the plurality of respective particle counts.

17. The system of claim 15, wherein each of the plurality of detection nodes is configured to determine the particle count within the respective air volume with at least a threshold particle count frequency of at least once per 5 minute interval.

18. The system of claim 15, wherein the plurality of detection nodes is spaced apart in a two-dimensional detection node array.

* * * * *